United States Patent
Davis et al.

(10) Patent No.: US 9,464,031 B2
(45) Date of Patent: *Oct. 11, 2016

(54) DEHYDROXYLATION OF AMINOALCOHOLS TO ALKYL AMINES

(71) Applicant: ANGUS Chemical Company, Buffalo Grove, IL (US)

(72) Inventors: Paul Davis, Pune (IN); Raj Deshpande, Pune (IN); George David Green, Cary, IL (US); Vandana Pandey, Pune (IN)

(73) Assignee: ANGUS CHEMICAL COMPANY, Buffalo Grove, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/652,214

(22) PCT Filed: Nov. 21, 2013

(86) PCT No.: PCT/US2013/071265
§ 371 (c)(1),
(2) Date: Jun. 15, 2015

(87) PCT Pub. No.: WO2014/099248
PCT Pub. Date: Jun. 26, 2014

(65) Prior Publication Data
US 2015/0329471 A1    Nov. 19, 2015

(30) Foreign Application Priority Data

Dec. 17, 2012 (IN) ............................ 3894/DEL/2012

(51) Int. Cl.
C07C 209/68 (2006.01)
(52) U.S. Cl.
CPC .................................. *C07C 209/68* (2013.01)
(58) Field of Classification Search
CPC ..................................................... C07C 209/68
See application file for complete search history.

(56) References Cited

FOREIGN PATENT DOCUMENTS

| DE | 12 04 682 | 11/1965 |
|----|-----------|---------|
| DE | 1204682   | * 11/1965 |

OTHER PUBLICATIONS

International Preliminary Report on Patentability issued on PCT/US2013/071265, mailed Jun. 23, 2015.
International Search Report and Written Opinion on PCT/US2013/071265, mailed Apr. 24, 2014.
Mitchell et al., "A Study of Reduction with Hydriodic Acid: Use in Micro Determinations of Hydroxyl Groups," J.Am. Chem. Soc. (1938), 60, pp. 2723-2726.

* cited by examiner

*Primary Examiner* — Shailendra Kumar
(74) *Attorney, Agent, or Firm* — Foley & Lardner LLP

(57) ABSTRACT

The present invention provides a process for producing alkyl amines by dehydroxylation of aminoalcohols. This provides an alternate reaction route for making alkyl amines, such as 2-methylpropane-2-amine and its derivatives.

20 Claims, No Drawings

DEHYDROXYLATION OF AMINOALCOHOLS TO ALKYL AMINES

CROSS-REFERENCE TO RELATED APPLICATIONS

This application is a 371 National Phase Application of PCT/US2013/071265, filed Nov. 21, 2013, which claims priority from Indian application serial number 3894/DEL/2012, filed Dec. 17, 2012, which are incorporated herein by reference in their entireties.

FIELD OF THE INVENTION

The present invention relates to a process for producing alkyl amines by dehydroxylation of aminoalcohols.

BACKGROUND OF THE INVENTION

Alkyl amines are useful in industries such as pharmaceutical, agriculture, rubbers, water treatment, paints and dyes, as well as for intermediates and starting materials for making other compounds.

Alkyl amines have been prepared from ammonia by alkylation with alcohols, in the presence of a catalyst, and followed by purification of the product. Alternatively alkyl amines may also be prepared by treatment of haloalkanes with ammonia and amines, however, the degree of alkylation is difficult to control. Another method for producing alkyl amines is the reduction of nitriles, by catalytic hydrogenation, to alkyl amines.

Preparation of alkyl amines by dehydroxylation of aminoalcohols has not yet been reported. Reductive dehydroxylation is known for activated alcohols, e.g., benzylic alcohols. It has not, however, been documented for aminoalcohols such as 2-amino-2-methyl-1-propanol (2-AMP).

Mitchell, et al., J. Am. Chem. Soc. (1938), 60, 2723, describes the use of hydroiodic acid (HI) for the conversion of polyols to alkanes. However, no mention of the application of such reaction chemistry to aminoalkanols is made in this journal article.

The ability to produce alkyl amines from alternative feedstocks, such as, aminoalcohols or aminopolyols, would be beneficial and is desired.

SUMMARY OF THE INVENTION

The present invention provides a dehydroxylation process for preparing an alkyl amine from an aminoalcohol comprising: (A) contacting a aminoalcohol with an iodine catalyst selected from hydroiodic acid and iodine, in a reaction zone, under hydrogen pressure; and (B) heating the reaction zone and contents to a reaction temperature between 50° C. and 250° C. to form the alkyl amine.

In some embodiments, the aminoalcohol is contacted with hydroiodic acid under hydrogen pressure, and the reaction temperature is between 100° C. and 200° C. In such embodiments, the aminoalcohol is 2-amino-2-methyl-1-propanol, the reaction temperature is between 120° C. and 200° C., and the alkyl amine produced is 2-methylpropan-2-amine.

In some embodiments, the aminoalcohol is contacted with iodine under hydrogen pressure, the reaction temperature is between 100° C. and 200° C., the aminoalcohol is 2-amino-2-methyl-1-propanol, and the alkyl amine produced is 2-methylpropan-2-amine.

DETAILED DESCRIPTION OF THE INVENTION

The following terms, phrases and meanings are used hereinafter.

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the component amounts of the composition and various process parameters such as, without limitation, reaction temperature and pressure.

The term "alkanolamines," as used herein, means compounds that have hydroxy (—OH) and amino (—$NH_2$, —NHR, and —$NR_2$, where R is a hydrogen, alkyl, aryl, etc.) functional groups on an alkane backbone.

The term "alkyl amines," as used herein, means compounds that one or more amino (—$NH_2$, —NHR, and —$NR_2$, where R is a hydrogen, alkyl, aryl, etc.) functional groups on an alkane backbone.

"Catalytic amount" and like terms, when applied to iodine catalysts, mean the amount of iodine catalyst required to promote, at a desired rate, the dehydroxylation reaction of a aminoalcohol to form the corresponding alkyl amine having the same number of carbon atoms as the starting aminoalcohol. The amount will vary dependent upon a variety of factors including, but not limited to, the nature of the reagents, the dehydroxylation conditions, the nature of the catalyst and the like.

"Dehydroxylation conditions" and like terms mean the temperature and pressure under which an aminoalcohol is converted to a alkyl amine in the presence of an iodine catalyst (i.e., hydroiodic acid (HI) or iodine ($I_2$)), under hydrogen pressure, with or without a solvent. These conditions are dependent upon a host of factors including, but not limited to, the aminoalcohol, which iodine catalyst is present, and the reaction temperature. Typically the temperature is up to 250° C., such as from 50 ° C. to 250° C., more typically from 100° C. to 190° C., or even from 120° C. to 190° C. Typically the pressure is 50 psi (345 kPa) to 2000 psi (13,790 kPa), such as 200 psi (1,379 kPa) to 1000 psi (6,895 kPa) or 200 psi (1,379 kPa) to 800 psi (5,516 kPa), or even 500 psi (3,447 kPa) to 1000 psi (6,895 kPa).

The present invention provides a dehydroxylation process for preparing an alyl amine from an aminoalcohol. More particularly, an aminoalcohol is contacted with an iodine catalyst, such as hydroiodic acid or iodine, under hydrogen pressure, in a reaction zone, which is then heated to a reaction temperature up to 210° C. to form the corresponding alkyl amine by dehydroxylation. Suitable hydrogen pressure is from 50 to 2000 psig (345 to 13,790 kPa), and preferably from 300 to 1000 psig (2,068 to 6,895 kPa).

The iodine catalyst is selected from the group consisting of hydroiodic acid (HI) or iodide ($I_2$). The iodine catalyst is typically present in a molar ratio of aminoalcohol to iodine of from 1:10 to 100:1, such as between 1:2 and 10:1, and preferably between 3:1 and 9:1.

A solvent is not required, but is recommended. Suitable solvents include solvents, such as, without limitation, water, acetic acid, propionic acid, and straight chain and branched isomers of butyric, pentanoic, and hexanoic acids, and mixtures thereof. Preferably, the solvent is polar, but this is not required.

The reaction temperature may be maintained by heating the reaction zone for up to 24 hours, preferably up to 12 hours, and more preferably up to 6 hours, but not less than 1 hour, preferably not less than 2 hours, and more preferably not less than 4 hours. The reaction temperature may be between 50° C. and 250° C., such as between 100° C. and 220° C., or between 160° C. and 220° C., or between 120° C. and 190° C., or between 170° C. and 200° C., or between 100° C. and 160° C.

Applicants have surprisingly discovered that it is possible to dehydroxylate aminoalcohols and aminopolyols to form corresponding alkyl amines, under conditions known and applied to produce N-alkylhydroxylamines from nitroalkanes.

The aminoalcohols useful in the practice of this invention may be, without limitation, selected from $C_1$-$C_{20}$ aminoalkanols. Particularly preferred are aminoethanol, 1-aminopropanol, and 2-aminopropanol, derivatives and combinations thereof. For example, without limitation, 2-amino-2-methyl-1-propanol (2-AMP) would be a derivative of 2-aminopropanol which is suitable for use in connection with the present invention.

It is noted that the dehydroxylation process of the present invention is also useful for converting aminopolyols to aminoalcohols and, then, to alkyl amines. For example, 2-amino-2-methyl-1,3-propandiol (AMPD) can be converted to 2-amino-2-methyl-1-propanol (2-AMP), which can then be further dehydroxylated to 2-methylpropan-2-amino (2-MPA).

In some embodiments of the dehydroxylation process of the present invention, an aminoalcohol is converted to an alkyl amine in the presence of hydroiodic acid, with a molar excess of hydroiodic acid, at reaction temperatures between 100° C. and 160° C., under hydrogen pressure.

In some embodiments, an aminoalcohol is converted to an alkyl amine in the presence of hydroiodic acid with a molar excess of the aminoalcohol, at reaction temperatures between 170° C. and 200° C., under hydrogen pressure.

Various embodiments of the process of the present invention will now be described in detail in connection with the following examples.

EXAMPLES

Key Terminology
2-AMP=2-amino-2-methyl-1-propane
Glacial acetic acid=undiluted or pure acetic acid
HI=hydroiodic acid General Experimental Procedure A 300 mL Hast-C Parr reactor was charged with a known amount of 2-NMP (70% in water), glacial acetic acid (80 mL), and hydrogen iodide (55% aqueous w/w Merck) or iodine (equivalent amount S.D. Fine-Chem Ltd). The autoclave was sealed, purged with nitrogen (200 psig) twice, and then pressurized to the desired pressure of hydrogen. Agitation was started and set at 1000 rpm. The reaction temperature was increased to the desired temperature and maintained for the required duration. At the end of reaction the autoclave was cooled to room temperature and a sample was collected for analysis.

Gas Chromatograph Analysis Procedure

The liquid samples were analyzed on Agilent 7890 GC. Agilent HP-5 (19091)-413) GC column (30 m×320 µm×0.25 µm) and the progress of the reaction monitored based on GC area %. The FID (flame ionization detector) was set at 280° C. and the injector port at 180° C. The oven temperature was set at 80° C. and hold for 2 minutes and further to 200° C. with temperature ramping of 10° C./min. The injection volume was 1 µL with split ratio of 25:1 and helium was used as carrier gas.

Example 1

Dehydroxylation of 2-AMP Using HI

Reaction condition: 2-AMP (0.044 moles), HI (0.024 moles), T (190° C.), Time (6 hours).
At the end of 6 hours, a 66% conversion of 2-AMP was obtained with 100% selectivity to 2-methylpropan-2-amine.

Example 2

Dehydroxylation of 2-AMP Using Iodine/$H_2$

Reaction condition: 2-AMP (0.078 moles), Iodine (0.0067 moles), T (150° C.), Time (6 hours). At the end of 6 hours, a 41% conversion of 2-AMP was obtained with 100% selectivity to 2-methylpropan-2-amine.

What is claimed is:
1. A dehydroxylation process for preparing an alkyl amine from an aminoalcohol comprising:
   (A) contacting the aminoalcohol with a dehydroxylation catalyst selected from the group consisting of hydroiodic acid and iodine, in a reaction zone, under hydrogen pressure; and
   (B) heating the reaction zone and contents to a reaction temperature between 50° C. and 250° C. to form the alkyl amine.
2. The dehydroxylation process according to claim 1, wherein said reaction temperature is maintained for a period of time up to 24 hours.
3. The dehydroxylation process according to claim 1, wherein the dehydroxylation catalyst is hydroiodic acid, and the reaction temperature is between 100° C. and 200° C.
4. The dehydroxylation process according to claim 3, wherein the aminoalcohol is 2-amino-2-methyl-1-propanol, the reaction temperature is between 120° C. and 200° C., and the alkyl amine produced is 2-methylpropan-2-amine.

5. The dehydroxylation process according to claim 1, wherein the dehydroxylation catalyst is iodine and the reaction temperature is between 100° C. and 200° C.

6. The dehydroxylation process according to claim 5, wherein the aminoalcohol is 2-amino-2-methyl-1-propanol and the alkyl amine produced is 2-methylpropan-2-amine.

7. The dehydroxylation process according to claim 1, wherein the pressure is from 50 psi to 2000 psi.

8. The dehydroxylation process according to claim 1, wherein the pressure is between 200 psi and 1000 psi.

9. The dehydroxylation process according to claim 1, wherein the molar ratio of aminoalcohol to dehydroxylation catalyst is 1:10 to 100:1.

10. The dehydroxylation process according to claim 1, wherein the molar ratio of aminoalcohol to dehydroxylation catalyst is 1:2 to 10:1.

11. The dehydroxylation process according to claim 1, wherein the process occurs in the presence of a solvent selected from the group consisting of water; acetic acid; propionic acid; straight chain and branched isomers of butyric, pentanoic, and hexanoic acids; and mixtures thereof.

12. The dehydroxylation process according to claim 1, wherein the reaction temperature is maintained for a period of time up to 6 hours.

13. The dehydroxylation process according to claim 1, wherein the reaction temperature is between 100° C. and 220° C.

14. The dehydroxylation process according to claim 1, wherein the aminoalcohol is a $C_1$-$C_{20}$ aminoalcohol.

15. The dehydroxylation process according to claim 1, wherein the aminoalcohol is selected from the group consisting of aminoethanol, 1-aminopropanol, 2-aminopropanol, derivatives thereof, and combinations of any two or more thereof.

16. The dehydroxylation process according to claim 1, wherein the aminoalcohol is 2-amino-2-methyl-1-propanol.

17. A dehydroxylation process for preparing an alkyl amine from an aminopolyol comprising:
 (A) contacting the aminopolyol with a dehydroxylation catalyst selected from the group consisting of hydroiodic acid and iodine, in a reaction zone, under hydrogen pressure;
 (B) heating the reaction zone and contents to a reaction temperature between 50° C. and 250° C. to form an aminoalcohol; and
 (C) continuing to heat the reaction zone and contents to form the alkyl amine.

18. The dehydroxylation process according to claim 17, wherein the aminopolyol is 2-amino-2-methyl-1,3-propandiol, the aminoalcohol is 2-amino-2-methyl-1-propanol, and the alkyl amine is 2-methylpropan-2-amine.

19. The dehydroxylation process according to claim 17, wherein the dehydroxylation catalyst is hydroiodic acid and the reaction temperature is between 100° C. and 220° C.

20. A dehydroxylation process for preparing an alkyl amine from an aminoalcohol comprising:
 (A) contacting the aminoalcohol with a dehydroxylation catalyst, optionally in the presence of solvent, in a reaction zone under a hydrogen pressure from 50 to 2000 psi, wherein
  the dihydroxylation catalyst is selected from the group consisting of hydroiodic acid and iodine;
  the molar ratio of aminoalcohol to dehydroxylation catalyst is 1:10 to 100:1; and
 (B) heating the reaction zone and contents to a reaction temperature between 100° C. and 220° C. to form the alkyl amine.

* * * * *